United States Patent [19]
Mönch

[11] Patent Number: 6,035,870
[45] Date of Patent: Mar. 14, 2000

[54] RINSING DEVICE FOR TROCAR SLEEVES

[75] Inventor: Harry Mönch, Knittlingen, Germany

[73] Assignee: Richard Wolf GmbH, Knittlingen, Germany

[21] Appl. No.: 09/078,742

[22] Filed: May 14, 1998

[30] Foreign Application Priority Data

Jul. 18, 1997 [DE] Germany ............................ 197 30 894

[51] Int. Cl.[7] .................................................. B08B 3/02
[52] U.S. Cl. ..................... 134/59; 134/169 C; 134/170; 422/297; 422/300
[58] Field of Search ............................ 134/166 C, 169 C, 134/168 C, 170, 135, 58, 200, 201; 422/297, 300

[56] References Cited

U.S. PATENT DOCUMENTS

| 3,771,539 | 11/1973 | Desantis | 134/170 |
|---|---|---|---|
| 4,281,674 | 8/1981 | Tanaka et al. | 134/170 |
| 4,299,244 | 11/1981 | Hirai | 134/170 |
| 4,552,728 | 11/1985 | Taylor | 422/300 |
| 4,708,153 | 11/1987 | Hambelton et al. | 134/170 |
| 4,763,678 | 8/1988 | Ott . | |
| 4,867,186 | 9/1989 | Otsuka | 134/135 |
| 5,137,689 | 8/1992 | Cantrell | 422/300 |
| 5,159,945 | 11/1992 | Bannon | 134/135 |
| 5,288,467 | 2/1994 | Biermaier | 134/170 |
| 5,346,075 | 9/1994 | Nichols et al. . | |
| 5,494,637 | 2/1996 | Barlow . | |
| 5,603,436 | 2/1997 | Chase | 134/170 |
| 5,749,385 | 5/1998 | Rochette et al. | 134/170 |
| 5,753,195 | 5/1998 | Langford et al. | 134/170 |
| 5,759,490 | 6/1998 | Malchesky | 422/297 |
| 5,882,589 | 3/1999 | Mariotti | 134/169 C |

FOREIGN PATENT DOCUMENTS

| 25 52 011 B2 | 11/1979 | Germany . | |
| 34 43912 A1 | 6/1986 | Germany . | |
| 1168035 | 6/1968 | United Kingdom | 134/170 |

*Primary Examiner*—Frankie L. Stinson
*Attorney, Agent, or Firm*—Akin, Gump, Strauss, Hauer & Feld, L.L.P.

[57] ABSTRACT

The invention relates to a rinsing device for trocar sleeves. A rinsing and accommodating tube for a trocar sleeve integrated into a basket system may be pivoted from a horizontal rinsing position into a vertical equipping and removal position by way of a pivoting part which is pivotably mounted on a base. All disassemblable individual parts of the trocar sleeve are mounted in a basket system with point contact free of areas shaded to rinsing and may after assembly of the individual parts remain in the basket for sterilization.

11 Claims, 3 Drawing Sheets

RINSING DEVICE FOR TROCAR SLEEVES

BACKGROUND OF THE INVENTION

The invention relates to a rinsing device for trocar sleeves with at least one base fixed onto a wire floor or perforated plate of a rinsing basket or likewise and with an elongate trocar sleeve rinsing and accommodating tube mounted on the base and distanced from this, which is in fluid connection with the base and comprises openings for rinsing fluid.

Apart from high technical demands also very high hygenic demands are made of the instrumentation of minimal invasive surgery, which has been increasingly applied in the last years. From the hygenic point of view an automized preparation by rinsing the instruments is necessary, since only in this way is a standardization of the preparation guaranteed. With this a manual preparation is to be avoided if at all possible. For a good and problem-free handling and also for hygenic aspects furthermore disassemblable instruments are required which only then make possible a standardization for an optimal preparation.

Generally there is the demand of the person responsible for the hygene of the instrumentation that all instruments and their parts are to be suitable for the automized preparation, since only thus can the standardization and a constantly present hygene with an adequate safety be guaranteed. The demand for disassemblable instruments which is so important for the hygene only brings reliable and adequate safety when the personnel is bound by the standardized preparation procedures.

A rinsing device for trocars and trocar sleeves must in the basket system provide special receptacles and holders for all instrument individual components, which are so formed that a mechanized preparation free of areas shaded to the rinsing is made possible.

A basket system, suitable for accommodating trocars to be rinsed and the individual parts of trocar sleeves, is due to the many individual components, best designed specially for rinsing and preparing the constituent parts of one or more trocars and trocar sleeves in the disassembled condition. In this manner it is ensured that all trocar parts remain controllably integrated in the operating procedure.

A known rinsing device comprises a rinsing basket for accommodating many different instruments and instrument parts. Longitudinally extended instruments and instrument shanks may be put therein in rows with an oblique resting with several connections for rinsing. Such a rinsing means has the disadvantage, that the manner of procedure and the arrangement is not fixed, but is determined by the operating personnel. Due to the oblique resting such rinsing baskets are also relatively large, and the preparation entails many factors of insecurity.

BRIEF SUMMARY OF THE INVENTION

It is therefore the object of the invention to so indicate a validatable mechanized instrument rinsing device for trocar sleeves with rigidly allocated holders for trocar sleeves in the container, that a rinsing basket carrying the goods to be rinsed or sterilized may be compact and that at the same time a more economical, safe and qualitatively high-grade rinsing procedure is possible.

For achieving the above object, a rinsing device for trocar sleeves with at least one base fixed to a wire floor or perforated plate of a rinsing basket or likewise, and with an elongate trocar sleeve rinsing and accommodating tube mounted on the base and distanced from this, which is in fluid connection with the base and comprises openings for rinsing fluid, is according to the invention characterized in that the rinsing and accommodating tube on the base may be pivoted from a horizontal rinsing position into an equipping and removal position.

By way of the pivotability of the rinsing and accommodating tube the trocar sleeve with the equipping in the perpendicular position may be simply stuck up and then in the horizontal position folded down. On the removal the trocar sleeve sterilized in the assembled condition may be comfortably removed in the perpendicular position. For this reason the rinsing basket may be compact, i.e. flat. A latching device engaging on the base and on the pivoting part ensures that the pivoting part in each case is latchingly fixed in the horizontal rinsing position and in the perpendicular equipping and removal position.

A spacer sitting on the end section of the rinsing and accommodating tube, there where this tube connects to the piivoting part, ensures that the trocar sleeve inserted onto the rinsing and accomodating tube is kept at a defined distance from the base.

On the spacer there are provided star-shaped and radially projecting spacer fins which in each case comprise an obliquely outwardly running rinsing bore which is in fluid connection with the inner volume of the rinsing and accommodating tube.

These fins have an oblique outer contour proceeding from the end of the rinsing and accommodating tube, so that the largest radial outer dimension from the longitudinal axis of the rinsing and accommodating tube is larger than the diameter of a trocar sleeve housing bearing on the spacer fins. Furthermore the obliqueness of the rinsing bores in the fins, seen from the base to the oppositely lying end of the rinsing and accommodating tube, is directed outwards. In this way an improved rinsing in the inner space of the cylindrical trocar sleeve housing lid can be achieved.

BRIEF DESCRIPTION OF THE DRAWINGS

The invention is hereinafter, also with regard to further features and advantages, described in more detail by way of one embodiment example illustrated in the drawing. There are shown.

DETAILED DESCRIPTION OF THE INVENTION

Figure 1:
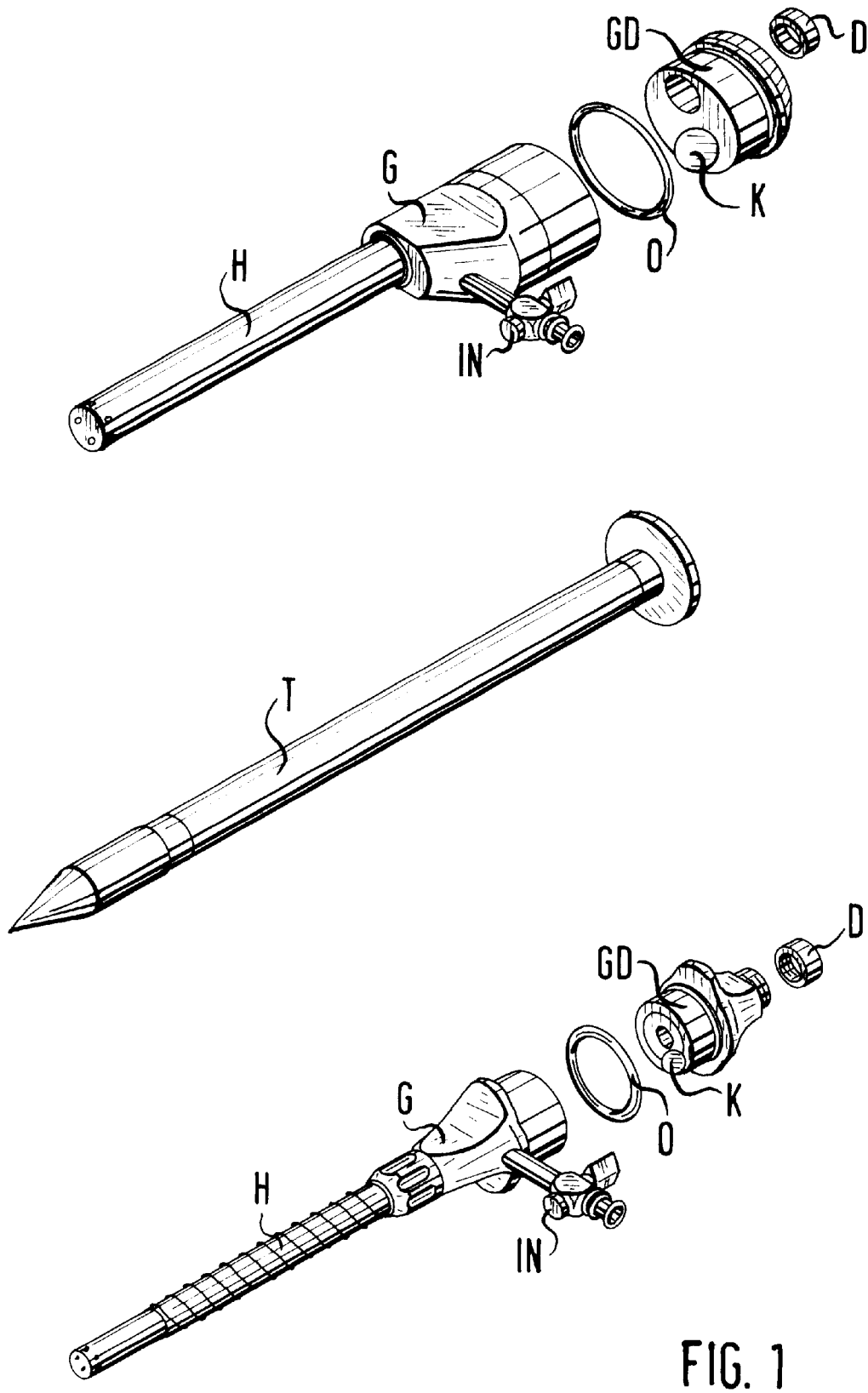
FIG. 1 perspectively, an embodiment form of a trocar with two differently formed trocar sleeves with a housing, a housing lid etc., which together with their individual elements can be prepared with the help of the rinsing device according to the invention.

Each of two embodiment forms of trocar sleeves with differing shank tube diameters represented in FIG. 1 comprise the following individual parts; a trocar sleeve with a housing and insufflation cock, a housing lid, an O-ring, a ball of a ball-magnet valve, a sealing cap and a trocar.

Such trocar sleeves can be applied and prepared in the rinsing device according to the invention.

Figure 2:
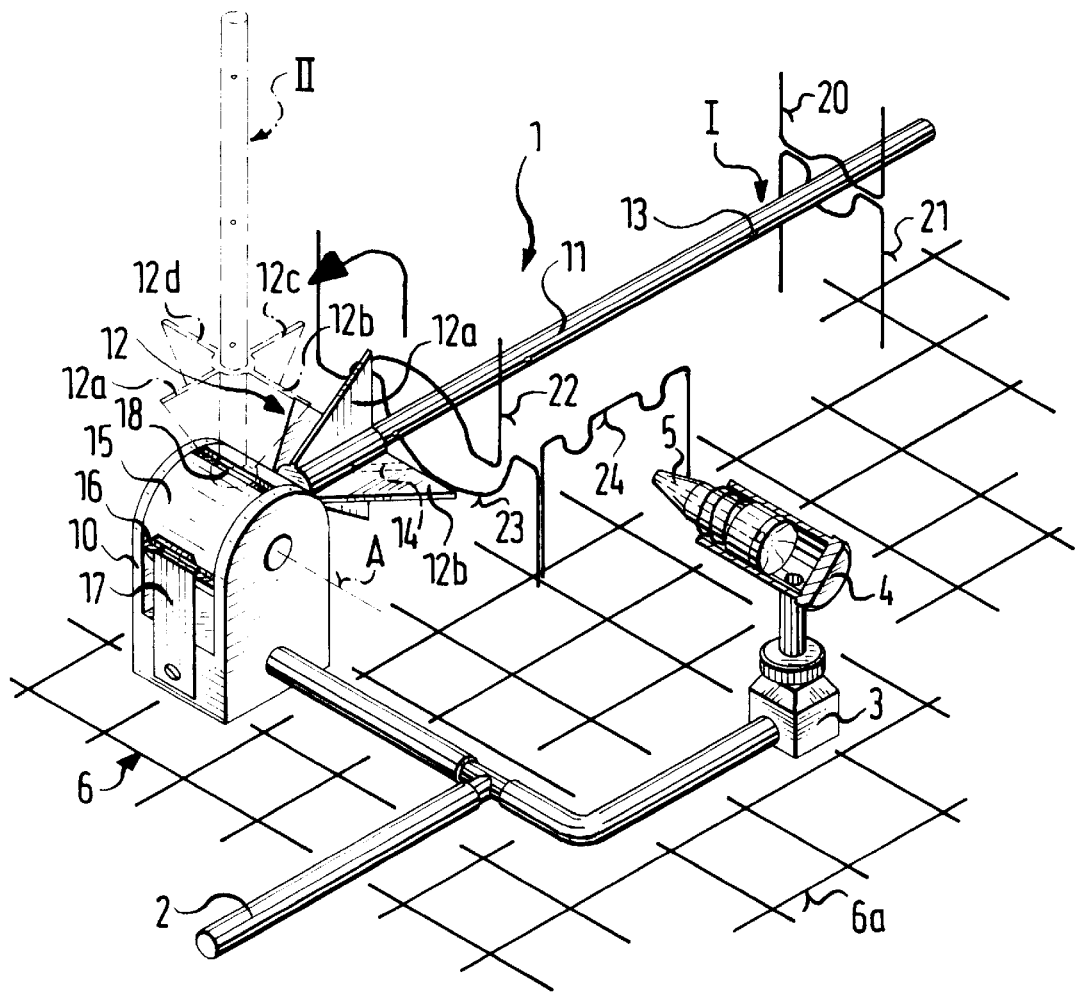
FIG. 2 perspectively, an embodiment form of a rinsing device according to the invention for a trocar sleeve housing and FIG. 3 a rinsing device according to the invention on rinsing a trocar sleeve housing and further supplementary details of the rinsing device.

FIG. 2 schematically shows an embodiment form of the rinsing device according to the invention indicated generally with the numeral 1, in the horizontal rinsing position I (unbroken lines) and in the perpendicular equipping and removal position II (dashed lines). All accommodating components shown are functionally complete individual holders. They are designed such that may be flexibly fastened according to the requirements on perforated plates or on the wire grid floor 6a of a rinsing basket 6, indicated in FIG. 2.

The instrument holders 20, 23 and 24 are so attached that they may securely accommodate the instrument with a point contact in a fixed manner. The counter holders 20 and 22 are arranged on the lid of the rinsing basket, which is not shown, so that with the lid layed down a circumferential fixation of the instrument, i.e. of the trocar sleeve is achieved (see also FIG. 3).

Via the fluid supply 2 all components which are in fluid connection with one another are supplied with rinsing fluid. The supply creates the direct connection to the preparation machine (not shown). With this the tubing connections may be flexibly extended corresponding to the number of accommodating components.

The rinsing device 1 for a trocar sleeve which is not shown in FIG. 2 comprises a base which can be fixed to the wire floor 6a of the rinsing basket, on which a trocar sleeve rinsing and accommodating tube 11 is pivotably mounted, this tube comprising openings 13 for the rinsing fluid.

Figure 3:
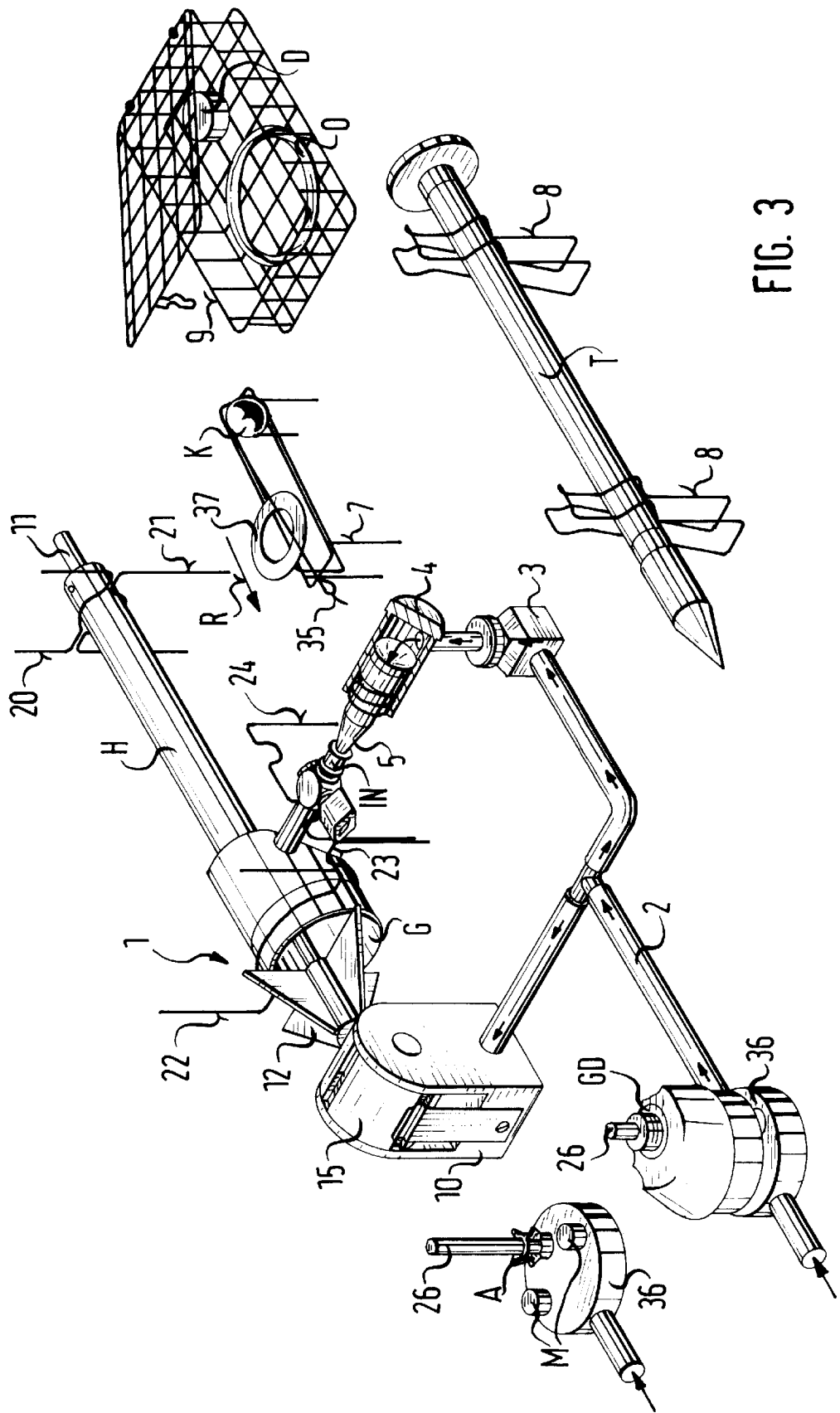

In the horizontal position I the trocar sleeve with the inserted rinsing and accommodating tube is furthermore fixed in each case between instrument holders fixed to the rinsing basket and to the container lid which covers this. The lower instrument holders 21, 23, 24 are fastened on the rinsing basket whilst the upper instrument holders 20, 22 are fastened on the container lid so that a point contact for the trocar sleeve is achieved (FIG. 3).

For pivoting the rinsing and the accommodating tube 11 on the base 10, a pivoting part 15 is pivotably mounted about a horizontal pivoting axis A, this pivoting part being releasably connected to the rinsing and accommodating tube 11 and being pivotable with this. A leaf spring 17 fastened to the base 10 comprises at its free end a latch 16 which resiliently engages into grooves 18 which are formed on the outer circumference of the pivoting part 15 parallel to the pivoting axis A. By way of this the pivoting part 15 with the rinsing and accommodating tube 11 fastened thereto in each case latches in the horizontal rinsing position I and in the perpendicular equipping and removal position II. Of course further latching positions in the form of additional grooves, e.g. in the 45° position may be provided.

The rinsing and accommodating tube 11 comprises on its end section connecting to the pivoting part 15 a star-shaped formed spacer in order to hold the trocar sleeve stuck onto the rinsing and accommodating tube 11 at a defined distance from the pivoting part 15. Four distance fins 12a–12d which are uniformly distanced in the circumferential direction and which protrude radially from the spacer are formed such that from the connection point of the rinsing and accommodating tube 11 they have outer edges running obliquely outwards, whose largest distance from the longitudinal axis of the rinsing and accommodating tube 11 is larger than the diameter of a trocar sleeve housing bearing thereon. In the fins 12a to 12d there is formed a fine rinsing bore 14 which as shown in FIG. 2, run obliquely and which improve the rinsing in the inner space of the cylindrical part of the trocar sleeve housing.

The rinsing device shown in FIG. 2 furthermore comprises an injection nozzle 4, 5 which injects rinsing fluid into an insufflation cock of the trocar sleeve housing which with a base 3 separate from the described base 10 can be attached to a suitable location of the wire floor 6a of the rinsing basket 6. A supply being in fluid connection with the common rinsing fluid supply 2 leads into the base 3 of the injection nozze and supplies rinsing fluid under pressure. The injection nozzle comprises a plunger 5 which is movably guided in the axial direction in a hollow cylinder 4 and which at its conical distal end is adapted to the shape of the insufflation cock and which can be so actuated by way of pressurized fluid led into the hollow cylinder 4 by way of the base 4, that the channel of the insufflation cock is sealed to the outside. The hollow cylinder 4 is fastened to the base 3 adjustable in height.

In FIG. 3 there is shown a trocar sleeve which is disassembled into its components which are inserted into, in each case the provided receptacles. There are indicated:

D: sealing cap
G: housing of the trocar sleeve
GD: housing lid
H: trocar sleeve
IN: insufflation cock
K: ball of the ball-magnet valve
O: O-ring
T: trocar In the manner already described by way of FIG. 2 the trocar sleeve H is accommodated by the rinsing and accommodation tube 11 and is accommodated between the instrument holders 20–24 with a point contact. The spacer fins 12a–12d bear on the edge of the trocar sleeve housing G, the trocar sleeve H is rinsed and the nozzle 4, 5 is docked onto the inner lumen of the insufflation cock IN. With this pressurized rinsing fluid is injected from the nozzle 4, 5 into the inner lumen of the insufflation cock IN.

The ball K of the ball-magnet valve is contained in a specially formed ball catch 7 which during the preparation serves for accommodating several balls for a mounting free of areas shaded to the rinsing. Normally the ball is magnetically held on the housing lid GD. For incorporating the ball K into the ball catch 7 the housing lid GD with the ball K stuck thereon is pressed onto the arcuate hole disk 37 so that the ball protrudes into the inner diameter of the hole disk. With this the safety spring 35 is pressed to the side. The housing lid is then pushed in the direction of arrow R by which means the ball K is dragged by the housing lid GD and slides into the ball catch 7. The ball catch 7 is designed for several balls. The safety spring 35 narrows the inner diameter to the hole disk. By way of this an undesired falling out of the ball K is prevented. For removing the ball K the housing lid with the bore is aligned to the ball. With this the magnet of the housing lid grasps the ball and the housing lid is pushed in the direction of the hole disk 37. During this the safety spring 35 slides to the side, and the ball may then be removed from the ball catch, wherein the ball assumes its defined position.

The ball catch 7 is conceived such that a depositing or removal of balls K is possible without any problem.

Wire form parts 8 which are fastened to the floor 6a of the illustrated rinsing basket 6 from a secure receptacle for the trocar T. Furthermore there is a small utensil basket 9 provided with a lid, which is rigidly incorporated into the basket system. In this all small components such as e.g. the sealing cap D or the O-ring O may be kept for rinsing, for which no special holders are provided.

For rinsing the housing lid GD there is provided an individual rinsing device 36 which contains a vertically projecting short rinsing tube 26. All above described wire formed parts and clips form a point-like contact which is free of areas shaded to the rinsing, for the individual parts of the trocar sleeve including the trocar. The housing lid receptacle 36 shown in FIG. 3 is provided with an adjusting and spacer part A at the foot point of the perpendicular rinsing tube 26. The fixation of the housing lid is effected with the fins projecting from the spacer A, which engage with point contact into the bore of the housing lid and which fix the rinsing tube 26 with the rinsing nozzles centrically to the inner wall of the housing lid. With two magnets M the housing lid GD is securely held.

FIGS. 2 and 3 in each case show the individual parts of only one trocar sleeve. When required the rinsing device according to the invention may however also serve the accommodation of several trocar sleeves or trocars or also be designed for accommodating endoscope shanks or likewise.

After the mechanized preparation the trocar is kept in the same basket system. For the sterilization the basket system is packet into foil and inserted into a sterilizer. In the operation room the rinsing and accommodation tube is brought into the vertical position, the trocar sleeve taken and the sealing cap stuck on. With a few hand grips the trocar is then ready for operation.

Concluding the rinsing device for trocar sleeves according to the invention has the following advantages:

In a basket system the mechanized preparation is carried out, and the assembled instrument for the sterilization (steam/gas) remains in the basket system where appropriate enclosed by a sterilization foil. The instrument and all disassemblable individual parts are securely mounted in special holders with a point contact and by way of this ensure a mechanized preparation free of areas shaded to the rinsing.

Narrow instrument accesses, in particular the inner lumen of the insufflation cock, are docked individually for the through-rinsing by way of an injection nozzle. The rinsing and accommodating tube equipped with the trocar sleeve to be rinsed may be folded from the horizontal rinsing position into a perpendicular position in a simple manner in order to be able to remove the trocar sleeve.

I claim:

1. A rinsing device for trocar sleeves with at least one base fixed onto a wire floor or perforated plate of a rinsing basket or likewise and with an elongate trocar sleeve rinsing and accommodating tube mounted on the base and distanced from this, which is in fluid connection with the base and comprises openings for rinsing fluid, wherein the rinsing and accommodating tube on the base may be pivoted from a horizontal rinsing position into an equipping and removal position.

2. A rinsing device according to claim 1, wherein on the base a pivoting part connected to the rinsing and accommodating tube is pivotably mounted about a horizontal axis and the equipping and removal position is vertical.

3. A rinsing device according to claim 2, wherein on the base and on the pivoting part a latching device is provided, which effects a latching of the pivoting part in each case in the horizontal rinsing position and in the perpendicular equipping and removal position.

4. A rinsing device according to claim 3, wherein the latching device has a leaf spring fastened on the base, which engages in the respective latching position into defined grooves on the pivoting part.

5. A rinsing device according to claim 1, wherein the rinsing and accommodating tube on its end section connecting to the pivoting part comprises a spacer which keeps the trocar sleeve stuck on the rinsing and accommodating tube at a defined distance from the pivoting part.

6. A rinsing device according to claim 5, wherein the spacer is star-shaped and comprises radially projecting spacer fins.

7. A rinsing device according to claim 6, wherein the spacer fins comprise rinsing bores which run obliquely outwards and are in fluid connection with the inner lumen of the rinsing and accommodating tube.

8. A rinsing device according to claim 6, wherein four spacer fins uniformly distanced in the circumferential direction of the rinsing and accommodating tube are provided, whose largest radial outer dimension from the longitudinal axis of the rinsing and accommodating tube is larger than the diameter of a trocar sleeve housing bearing thereon, and that the obliqueness of the rinsing bores in the fins, seen from the base to the oppositely lying end of the rinsing and accommodating tube, is directed outwardly.

9. A rinsing device according to claim 1, wherein a nozzle injecting rinsing fluid into an insufflation cock of the trocar sleeve housing is provided separately from the base.

10. A rinsing device according to claim 1, wherein on the rinsing basket and/or on a container lid covering this rinsing basket there are provided fixable instrument holders which keep the rinsing and accommodating tube and/or an insufflation cock distanced from the trocar sleeve housing in the rinsing position.

11. A rinsing device according to claim 1, wherein the rinsing and accommodating tube and the spacer are releasably fastened to the pivoting part.

* * * * *